United States Patent
Carpenter et al.

(10) Patent No.: US 7,550,971 B2
(45) Date of Patent: Jun. 23, 2009

(54) METHODS OF IN VITRO ANALYSIS USING TIME-DOMAIN NMR SPECTROSCOPY

(75) Inventors: Scott E. Carpenter, Middlebury, IN (US); Thomas P. Benson, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 8 days.

(21) Appl. No.: 11/794,920

(22) PCT Filed: Jan. 13, 2006

(86) PCT No.: PCT/US2006/001327

§ 371 (c)(1),
(2), (4) Date: Jul. 9, 2007

(87) PCT Pub. No.: WO2006/076631

PCT Pub. Date: Jul. 20, 2006

(65) Prior Publication Data

US 2008/0088308 A1    Apr. 17, 2008

Related U.S. Application Data

(60) Provisional application No. 60/643,896, filed on Jan. 14, 2005.

(51) Int. Cl.
*G01V 3/00* (2006.01)
(52) U.S. Cl. .................... 324/307; 324/300
(58) Field of Classification Search ........... 324/307, 324/300
See application file for complete search history.

(56) References Cited

U.S. PATENT DOCUMENTS 4,875,486 A    10/1989    Rapoport et al. ............ 128/653

(Continued)

FOREIGN PATENT DOCUMENTS

WO    WO 2004/040407 A2    5/2004

(Continued)

OTHER PUBLICATIONS

Written Opinion of the International Searching Authority corresponding to co-pending International Patent Application No. PCT/US2006/001327, European Patent Office, dated Jun. 7, 2006, 5 pages.

(Continued)

*Primary Examiner*—Louis M Arana
(74) *Attorney, Agent, or Firm*—Nixon Peabody LLP

(57) ABSTRACT

An in vitro method of determining an analyte concentration of a sample includes placing the sample into a low-field, bench-top time-domain nuclear magnetic resonance (TD-NMR) spectrometer. The NMR spectrometer is tuned to measure a selected type of atom. A magnetic field is applied to the sample using a fixed, permanent magnet. At least one 90 degree radio-frequency pulse is applied to the sample. The radio-frequency pulse is generally perpendicular to the magnetic field. The 90 degree radio-frequency pulse is removed from the sample so as to produce a decaying NMR signal. The decaying NMR signal is measured at a plurality of times while applying a plurality of 180 degree refocusing radio-frequency pulses to the sample. The analyte concentration is calculated from the plurality of measurements associated with the decaying NMR signal and a selected model.

20 Claims, 2 Drawing Sheets

U.S. PATENT DOCUMENTS

| | | | | |
|---|---|---|---|---|
| 5,072,732 | A | 12/1991 | Rapoport et al. | 128/653.2 |
| 5,254,460 | A | 10/1993 | Josephson et al. | 435/7.25 |
| 5,377,674 | A | 1/1995 | Kuestner | 128/633 |
| 5,675,253 | A | 10/1997 | Smith et al. | 324/306 |
| 5,685,300 | A | 11/1997 | Kuenstner | 128/632 |
| 6,163,154 | A | 12/2000 | Anderson et al. | 324/320 |
| 6,194,900 | B1 | 2/2001 | Freeman et al. | 324/321 |
| 6,404,197 | B1 | 6/2002 | Anderson et al. | 324/311 |
| 7,316,649 | B2 * | 1/2008 | Fuller | 600/365 |
| 2004/0142496 | A1 | 7/2004 | Nicholson et al. | 436/536 |
| 2007/0116602 | A1 * | 5/2007 | Lee | 422/82.01 |

FOREIGN PATENT DOCUMENTS

WO    WO 2004/075734 A2    9/2004

OTHER PUBLICATIONS

International Search Report corresponding to co-pending International Patent Application No. PCT/US2006/001327, European Patent Office, dated Jun. 7, 2006, 4 pages.

* cited by examiner

METHODS OF IN VITRO ANALYSIS USING TIME-DOMAIN NMR SPECTROSCOPY

CROSS-REFERENCE TO RELATED APPLICATIONS

This application claims priority to Application No. 60/643,896 filed on Jan. 14, 2005, which is incorporated by reference in its entirety.

FIELD OF THE INVENTION

The present invention relates generally to methods of determining an analyte concentration of a sample. More particularly, the present invention relates to methods of determining an analyte using a low-field, time-domain nuclear magnetic resonance (NMR) spectrometer.

BACKGROUND OF THE INVENTION

The quantitative determination of analytes in body fluids is of great importance in the diagnoses and maintenance of certain physiological abnormalities. Some non-limiting examples of analytes that may be monitored in certain individuals include cholesterol (e.g. HDL, LDL, total), triglycerides, globulin, albumin, total protein, blood urea nitrogen, creatinine, and alkaline phosphastase.

Nuclear magnetic resonance (NMR) spectroscopy is an analytical and diagnostic technique that is used for structural and quantitative analysis of one or more analytes in a sample. One specific type of NMR is time domain nuclear magnetic resonance (TD-NMR). TD-NMR spectrometers are used for spin-lattice ($T_1$) and spin-spin ($T_2$) relaxation measurements. NMR spectrometers have been used to analyze body fluid samples, such as blood plasma. NMR is based on nuclear magnetic properties of certain elements and isotopes of those elements. One such element that is commonly analyzed by NMR is hydrogen, which has a single proton and an intrinsic nuclear spin. Hydrogen is present in many analytes of interest and has high natural abundance. When hydrogen nuclei are placed in a magnetic field, they adopt one of two allowed orientations. Therefore, the resulting magnetic moment can be aligned with the magnetic field or opposed to the magnetic field. The two orientations are separated by an amount of energy that depends on the strength of the magnetic field and the strength of the interaction between the hydrogen nucleus and the field. The energy difference may be determined by applying an electromagnetic pulse at a characteristic resonance frequency, which causes the nuclei aligned with the field (lower energy state) to align against the field (higher energy state).

The resonance frequency, ν, of a hydrogen nucleus is dependent on the strength of the magnetic field, Bo, and is given by:

$$\nu = \gamma B_o / 2\pi$$

where ν is in units of MHz, $B_o$ is in units of tesla (T) and γ is the fundamental gyromagnetic ratio for hydrogen ($^1$H) and is equal to $267.512 \times 10^6$ rad $T^{-1}s^{-1}$. Magnetic field strengths commonly used for NMR spectroscopy are in the range of from 1.4 to 14.1 T, corresponding to hydrogen resonance frequencies of from 60 to 600 MHz. Since hydrogen is the most common nucleus studied, NMR spectrometers are often classified by their hydrogen resonance frequencies instead of their actual magnetic field strengths.

The two most common types of magnets used in NMR spectrometers are permanent magnets and superconducting magnets. Although permanent magnets provide acceptable field stability and are less costly, the field strength is limited to approximately 1.4 T (60 MHz).

In contrast, superconducting magnets can provide much higher fields in the range of from about 4.7 to about 18.8 T (from 200 to 800 MHz). It is important to remember that the resonance frequencies of hydrogen nuclei, as well as other non-identical nuclei, are proportional to the field strength. Neighboring nuclei, in the same molecule or in the solvent, may greatly impact the resonance frequency of a particular hydrogen nucleus. Therefore, to obtain characteristic NMR spectra with high resolution, it is desirable to use the higher magnetic fields achieved with superconducting magnets. Unfortunately, NMR systems that utilize superconducting magnets are very expensive, require cryogenic cooling with liquid nitrogen and liquid helium, and are very large (commonly occupying an entire room). In addition to field strength, the stability and homogeneity of the magnetic field should be controlled to obtain high-quality NMR spectra. High-field NMR spectrometers also employ special locking electronics to compensate for small field instabilities. In the sample probe, additional electronic hardware is used to control the homogeneity of the magnetic field by a process called shimming.

Additionally, the resulting high-resolution NMR spectra are complex and must be interpreted by a highly-trained scientist. The individuals who operate the high-resolution NMR equipment need to be well-trained. High-resolution NMR spectroscopy typically involves acquiring a complete spectrum and identifying peaks for qualitative and quantitative analysis.

Therefore, it would be desirable to provide a method of determining the concentration of one or more analytes using NMR that provides lower costs and is a convenient method to use without requiring highly-trained operators or scientists.

SUMMARY OF THE INVENTION

According to one method, an analyte concentration of a sample is determined in vitro by placing the sample into a low-field, bench-top time-domain nuclear magnetic resonance (TD-NMR) spectrometer. The NMR spectrometer is tuned to measure a selected type of atom. A magnetic field is applied to the sample using a fixed, permanent magnet. At least one 90 degree radio-frequency pulse is applied to the sample. The 90 degree radio-frequency pulse is generally perpendicular to the magnetic field. The 90 degree radio-frequency pulse is removed from the sample so as to produce a decaying NMR signal. The decaying NMR signal is measured at a plurality of times while applying a plurality of 180 degree refocusing radio-frequency pulses to the sample. The analyte concentration is calculated from the plurality of measurements associated with the decaying NMR signal and a selected model.

DETAILED DESCRIPTION OF THE ILLUSTRATED EMBODIMENT

The present invention is directed to a method of using a time-domain nuclear magnetic resonance (TD-NMR) spectrometer to determine the analyte concentration of a sample. The method is done in vitro and may be performed without using reagents. The term, in vitro, is defined herein as being an artificial environment outside the living organism (e.g., a petri dish or test tube). The present invention is anticipated to be used in hospitals and clinics, but it is contemplated that it may be used in other locations.

Some non-limiting examples of analytes that may be monitored in certain individuals include glucose, cholesterol (e.g. HDL, LDL, total), triglycerides, globulin, albumin, total protein, blood urea nitrogen, alkaline phosphastase, and creatinine. The present invention is not limited, however, to these specific analytes. The analytes may be in, for example, body fluid such as a blood serum sample, a blood plasma sample or a urine sample.

The spectrometer is a low-field, TD-NMR spectrometer. The term "low-field" as defined herein is a magnetic field being generally less than 1.4 T (tesla). TD-NMR spectrometers employ at least one fixed, permanent magnet, and hydrogen resonance frequencies of 10, 20 and 60 MHz are common. According to one embodiment, the TD-NMR spectrometer includes a magnetic field less than 1.4 T and does not include shimming or locking electronics or hardware.

TD-NMR spectrometers used in the present invention measure spin-spin ($T_2$) relaxation. Information about analytes is obtained directly from the $T_2$ relaxation signals or portions thereof. The TD-NMR spectrometer is a bench-top instrument, which means that the spectrometer may be operated while positioned on or to a bench. The bench-top TD-NMR spectrometer may be of different sizes.

The TD-NMR spectrometer is tuned to measure a selected type of atom. For example, it is contemplated that the TD-NMR spectrometer may be used to measure atoms such as hydrogen, fluoride, and phosphorous. It is desirable, however, for the TD-NMR spectrometer to be tuned to measure hydrogen because of its abundance.

The TD-NMR spectrometer includes a fixed permanent magnet and does not require the use of reagents. It is contemplated that an NMR contrast agent may be added to the sample to enhance the detection of the selected analyte. It is contemplated that the TD-NMR spectrometer, however, may include more than one fixed, permanent magnet.

Figure 1:
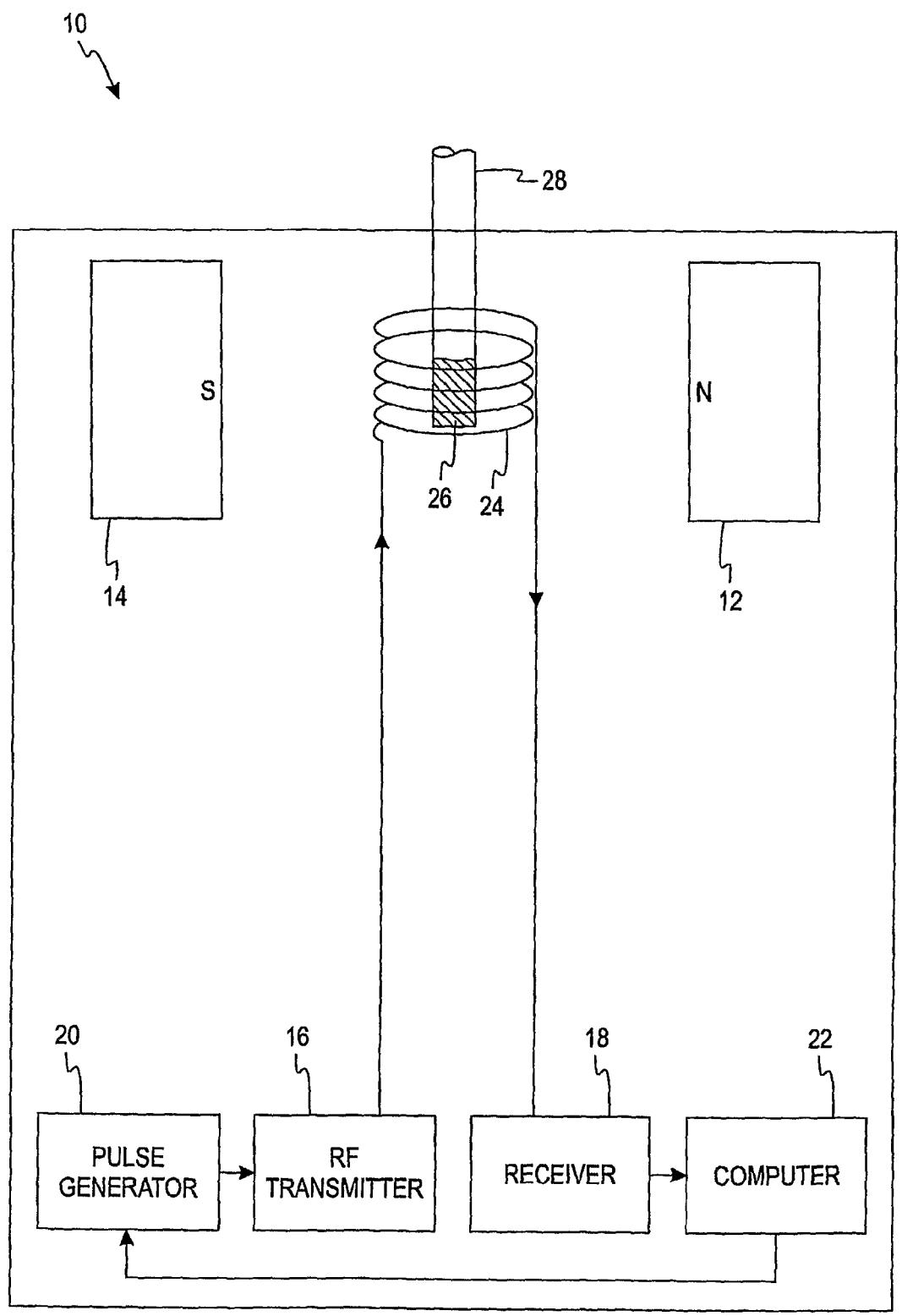
FIG. 1 is a front view of an NMR spectrometer according to one embodiment.

Referring to FIG. 1, a spectrometer 10 is shown according to one embodiment. The spectrometer 10 includes a first permanent magnetic 12, a second permanent magnetic 14, an RF transmitter 16, a receiver 18, a pulse generator 20, a computer 22 and an RF coil 24. The first and second permanent magnets 14,16 provide a magnetic field. The pulse generator 20 triggers the RF transmitter 14, which outputs radio-frequency pulses to the RF coil 24 and eventually to a sample 26 in a sample tube 28. The receiver 18 receives and converts the decaying NMR signals to a digitized form. The computer 22 uses the digitized signals from the receiver to calculate the analyte concentration.

One example of a TD-NMR spectrometer that may be used is a 20 MHz bench-top Bruker Minispec NMR spectrometer. The Bruker Minispec TD-NMR spectrometer has a 10 mm probe and a fixed 0.47 tesla magnet stabilized at 40° C. To control homogeneity, the temperature of the magnet may be precisely controlled such as to the nearest one-thousandth of a degree. The present invention, however, is not limited to this particular TD-NMR spectrometer. It is contemplated that other TD-NMR spectrometers may be used in the methods of the present invention.

According to the present invention, an analyte concentration of a sample is determined using an TD-NMR spectrometer and is performed in vitro. The analyte concentration of the sample may be determined in the absence of reagents. Information about analytes is obtained directly from the $T_2$ relaxation signals or portions thereof.

Figure 2:
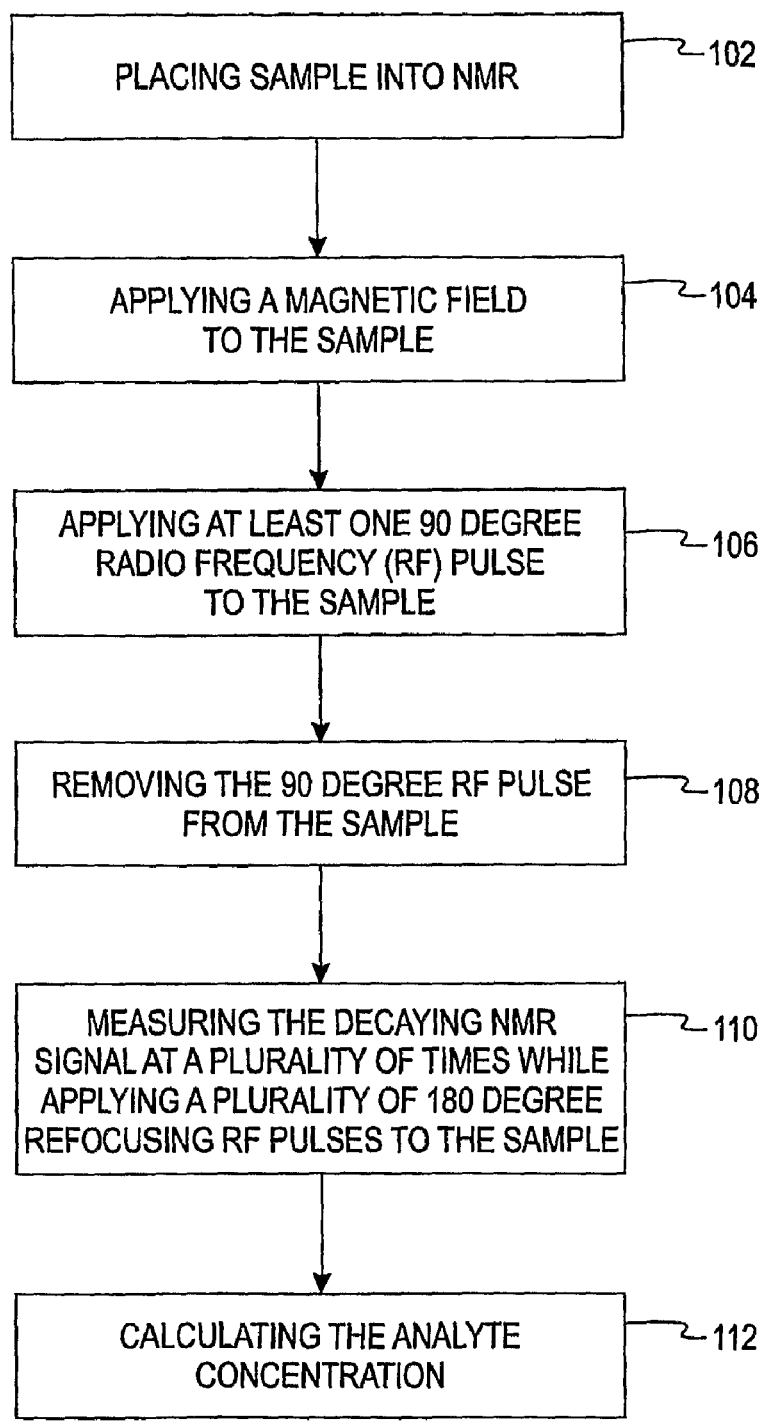
FIG. 2 is a flowchart of determining an analyte concentration according to one method.

Referring to FIG. 2, an in vitro method of determining an analyte concentration of a sample comprises the step 102 of placing a sample into an NMR spectrometer. In step 104, a magnetic field is applied to the sample. In step 106, at least one 90 degree radio-frequency (RF) pulse is applied to the sample. In step 108, the 90 degree radio-frequency pulse is removed from the sample so as to produce a decaying NMR signal. In step 110, the decaying NMR signal is measured at a plurality of times while applying a plurality of 180 degree refocusing radio-frequency pulses to the sample. In step 112, the analyte concentration is calculated from the plurality of measurements associated with the decaying NMR signal and a selected model.

According to another method, a sample is placed into a low-field, time-domain nuclear magnetic resonance (TD-NMR) spectrometer. For example, the sample may be placed into the TD-NMR spectrometer by placing a few milliliters of sample into a 10-mm diameter sample tube, which is then inserted into the spectrometer probe. The tube is typically a generally round shape, but it is contemplated that the tube may be of other shapes.

One example of a sample size that may be used is two milliliters of a blood serum sample, a blood plasma sample or other body fluids such as urine. It is contemplated that the TD-NMR spectrometer may be designed to have different sample sizes, which may result in an underfill or overfill condition relative to the coil. Using, for example, a Bruker Minispec TD-NMR spectrometer, a sample size of two milliliters (or greater) results in an overfill condition. In an overfill condition, the sampled volume is determined by the coil geometry. Therefore, the $T_2$ relaxation measurements of multiple samples analyzed in two or more milliliter quantities may be relatively compared and used for calibration. However, if quantities less than two milliliters are used, the sample volume does not completely fill the coil, which results in an under fill condition. Since the resulting $T_2$ relaxation profile will depend upon the absolute amount of sample in the coil, it is necessary to weigh each sample before analysis with the TD-NMR spectrometer. The resulting $T_2$ signal for each sample is divided by the weight of that sample. The adjusted $T_2$ measurements may then be used for comparison and calibration. When working with small sample volumes in an under fill situation, it is desirable to have at least enough sample to produce an NMR signal that is at least three times greater than the noise of the measurement.

The NMR spectrometer is tuned to measure at least one selected type of atom. The at least one selected type of atom may include hydrogen, fluoride, or phosphorous.

A first magnetic field is applied to the sample using a fixed, permanent magnet. The term "fixed" refers to the spacing being constant between the magnet and the sample, and the term "permanent" means that an intrinsic naturally-occurring magnetic field is associated with the magnet. Before the first magnetic field is applied, the nuclear magnetic moments of each proton (e.g., a hydrogen proton) are randomly oriented. After the first magnetic field is applied, a number of the nuclear magnetic moments of the protons orient themselves with the field, while a smaller number orient themselves against the first magnetic field. A net magnetization for the sample develops since the number of nuclear magnetic moments in each direction is not equal.

At least one radio-frequency (RF) pulse is applied to the sample to detect the sample's net magnetization. The radio-frequency pulse is generally perpendicular (i.e., about 90 degrees) to the first magnetic field and creates a second magnetic field. This radio-frequency pulse may be referred to as an excitation RF pulse. One method for accomplishing this radio-frequency pulse is by applying an alternating voltage across the ends of an NMR probe that induces an alternating magnetic field throughout the sample. Because the second magnetic field created by the RF pulse rotates the nuclear magnetic moments that had been oriented with or against the first magnetic field, the net magnetization of the sample is then no longer oriented in the same direction as the first magnetic field. After the individual magnetic moments are oriented by applying the RF pulse, they precess about the axis of the second magnetic field at a frequency that is dependent on the field strength. The precession of these spins generates a small oscillating magnetic field that is detected as an alternating current in a detection coil.

The RF pulse is removed from the sample so as to produce a decaying NMR signal. This causes the selected protons to return to their equilibrium condition through various relaxation processes. The precession frequency of each proton is dependent on the local field strength. Since the field of the first magnetic field is not uniform, sample protons can experience different field strengths. As each proton is in a different magnetic field due to its nearest neighbors, each magnetic moment precesses at a slightly different frequency. This difference in precession frequencies causes the precession of the individual moments to dephase. To compensate for the loss of phase coherence due to inhomogeneity in the first magnetic field, a plurality of 180 degree refocusing RF pulses is applied to the sample in order to measure the decaying NMR signal. The rate of decay is characterized by the spin-spin relaxation time, $T_2$. The sequence of the RF pulses applied to the sample follows the Carr-Purcell pulse sequence.

Relaxation produces a decaying NMR signal that is characteristic of the sample. The shape of the overall signal is the convolution of the decays representing all unique proton environments in the sample. The decaying NMR signal is measured at a plurality of times. The analyte concentration is calculated directly from the plurality of measurements of the decaying NMR signal.

To determine the concentration of an analyte in a sample, the NMR spectrometer is calibrated. Specifically, the analyte concentration in a sample is determined by applying a selected calibration model for the particular analyte to the plurality of signals associated with the decaying NMR relaxation signal. It is contemplated that several models may be used to calibrate the NMR spectrometer. One such example of a calibration method is described below.

According to one method, a selected calibration model for a specific analyte may be developed by first measuring the NMR relaxation for a plurality of samples, known as the calibration set. The measurements are performed of the range of the interest for the desired analyte. The analyte concentration in these samples may also be determined independently by a second reference method. One selected model that may be used a multivariate calibration model that uses for example chemometric techniques.

Chemometric techniques, such as, but not limited, to partial least squares (PLS) or principal components regression (PCR) may be used to develop a predictive model for the analyte of interest using the samples belonging to the calibration set. In such an analysis, the plurality of points comprising the relaxation for each sample is used as the X-matrix and the reference analyte concentrations for each sample comprise the Y-matrix.

The plurality of NMR signals comprising the NMR relaxation may be used directly or preprocessed in a number of ways. According to one method, all of the plurality of NMR signals are used without any processing. According to another method, a subset of the plurality of NMR signals are used without any processing.

The signal may be modified by applying techniques wherein the plurality of measurements includes data that is representative of the original measurements after preprocessing for smoothing. The plurality of measurements may include a subset of the data that is representative of the original measurements after preprocessing for smoothing. One example of a smoothing technique is Savitsky-Golay smoothing.

The signal may be fitted to various polynomials, such as, but not limited to, a exponential functional fit or a biexponential functional fit. In such cases, the X-matrix uses the transformed NMR relaxation. Alternatively, only a subset of the plurality of the original or transformed NMR signals may be selected for analysis. A number of chemometric procedures to be used for selecting subsets are known to those skilled in the art.

A mulivariate calibration model using a chemometric technique such as PLS is developed using the samples of the calibration set through a process known as cross-validation. A portion of the samples comprising the calibration set, known as the training set, is used to develop a model for the analyte of interest. Models with an increasing number of PLS factors are constructed to predict the analyte reference values (Y-matrix) using the NMR relaxation data, processed or otherwise (X-block).

The calibration models are validated using the remaining members of the calibration set referred to as the test set. The calibration models, as specified by a set of regression components for a specific number of PLS factors, are applied to the NMR relaxation data for the samples in the test set. The error between the predicted analyte value (x pred) and the reference value (x ref) for each sample in the test set may be calculated for each calibration model. To assess the quality of the calibration model, it is customary to use a statistic such as the standard error of cross validation (SECV) given by $$SECV = [\Sigma(x_{pred} - x_{ref})/n-k)]^{1/2}$$

where n=number of samples in the test set; and k=number of PLS factors in the model.

The calibration process may be repeated an iterative number of times with different members of the calibration set assigned to either the training or test set.

The optimum model is one that minimizes the prediction error for the samples of the test set, but contains a minimum number of PLS factors. Statistical tests may be applied to determine whether the improvement in the prediction error with an increase in the number of PLS factors is statistically significant.

After the proper number of PLS factors is determined through the cross validation process, a final calibration model is developed using the entire sample set of calibration samples.

The calibration model, consisting of a set of regression coefficients, may be applied to the plurality of the NMR signals comprising the relaxation of a new sample to predict the analyte concentration of interest.

Alternative Process A

An in vitro method of determining an analyte concentration of a sample, the method comprising the acts of:

placing the sample into a low-field, bench-top time-domain nuclear magnetic resonance (TD-NMR) spectrometer, the NMR spectrometer being tuned to measure a selected type of atom;

applying a magnetic field to the sample using a fixed, permanent magnet;

applying at least one 90 degree radio-frequency pulse to the sample, the radio-frequency pulse being generally perpendicular to the magnetic field;

removing the 90 degree radio-frequency pulse from the sample so as to produce a decaying NMR signal;

measuring the decaying NMR signal at a plurality of times while applying a plurality of 180 degree refocusing radio-frequency pulses to the sample; and calculating the analyte concentration from the plurality of measurements associated with the decaying NMR signal and a selected model.

Alternative Process B

The method of process A wherein the sample is a body fluid.

Alternative Process C

The method of process B wherein the sample is a blood plasma sample.

Alternative Process D

The method of process B wherein the sample is a blood serum sample.

Alternative Process E

The method of process B wherein the sample is a urine sample.

Alternative Process F

The method of process A wherein the analyte is selected from the group consisting of glucose, cholesterol, triglycerides, albumin, blood urea nitrogen, alkaline phosphastase, and creatinine.

Alternative Process G

The method of process A wherein the method is a reagent-less method.

Alternative Process H

The method of process A wherein the method includes adding an NMR contrast agent to the sample to enhance the detection of the selected analyte.

Alternative Process I

The method of process A wherein the selected type of atom is hydrogen, fluoride, or phosphorous.

Alternative Process J

The method of process I wherein the selected type of atom is hydrogen.

Alternative Process K

The method of process A wherein the NMR spectrometer includes a permanent magnet less than about 1.4 tesla in the absence of hardware or electronics for locking or shimming.

Alternative Process L

The method of process A wherein the selected model is a multivariate calibration model.

Alternative Process M

The method of process L wherein the multivariate calibration model uses a chemometric technique.

Alternative Process N

The method of process M wherein the chemometric technique uses partial least squares (PLS).

Alternative Process O

The method of process M wherein the chemometric technique uses principal components regression (PCR).

Alternative Process P

The method of process A wherein the plurality of measurements is all of the measurements in the absence of processing.

Alternative Process Q

The method of process A wherein the plurality of measurements is a subset of all of the measurements in the absence of processing.

Alternative Process R

The method of process A wherein the plurality of measurements includes data that is representative of the original measurements after preprocessing for smoothing.

Alternative Process S

The method of process A wherein the plurality of measurements includes a subset of data that is representative of the original measurements after preprocessing for smoothing.

Alternative Process T

The method of process A wherein the plurality of measurements includes data that is representative of the original measurements after preprocessing by fitting to a function.

Alternative Process U

The method of process T wherein the original measurements are preprocessed using an exponential functional fit.

Alternative Process V

The method of process T wherein the original measurements are preprocessed using a biexponential functional fit.

Alternative Process W

The method of process T wherein the plurality of measurements includes a subset of data that is representative of the original measurements after preprocessing by fitting to a function.

Alternative Process X

The method of process W wherein the original measurements are preprocessed using an exponential functional fit.

Alternative Process Y

The method of process W wherein the original measurements are preprocessed using a biexponential functional fit.

While the invention is susceptible to various modifications and alternative forms, specific methods thereof have been shown by way of example in the drawings and will herein be described in detail. It should be understood, however, that it is not intended to limit the invention to the particular methods disclosed but, on the contrary, the intention is to cover all modifications, equivalents, and alternatives falling within the spirit and scope of the invention as defined by the appended claims.

The invention claimed is:

1. An in vitro method of determining an analyte concentration of a sample, the method comprising the acts of:

placing the sample into a low-field, bench-top time-domain nuclear magnetic resonance (TD-NMR) spectrometer, the NMR spectrometer being tuned to measure a selected type of atom;

applying a magnetic field to the sample using a fixed, permanent magnet;

applying at least one 90 degree radio-frequency pulse to the sample, the radio-frequency pulse being generally perpendicular to the magnetic field;

removing the 90 degree radio-frequency pulse from the sample so as to produce a decaying NMR signal;

measuring the decaying NMR signal at a plurality of times while applying a plurality of 180 degree refocusing radio-frequency pulses to the sample; and calculating the analyte concentration from the plurality of measurements associated with the decaying NMR signal and a selected model.

2. The method of claim 1, wherein the sample is a body fluid.

3. The method of claim 2, wherein the sample is a blood plasma sample.

4. The method of claim 2, wherein the sample is a blood serum sample.

5. The method of claim 2, wherein the sample is a urine sample.

6. The method of claim 1, wherein the analyte is selected from the group consisting of glucose, cholesterol, triglycerides, albumin, blood urea nitrogen, alkaline phosphastase, and creatinine.

7. The method of claim 1, wherein the method is a reagentless method.

8. The method of claim 1, wherein the method includes adding an NMR contrast agent to the sample to enhance the detection of the selected analyte.

9. The method of claim 1, wherein the selected type of atom is hydrogen, fluoride, or phosphorous.

10. The method of claim 1, wherein the NMR spectrometer includes a permanent magnet less than about 1.4 tesla in the absence of hardware or electronics for locking or shimming.

11. The method of claim 1, wherein the plurality of measurements is all of the measurements in the absence of processing.

12. The method of claim 1, wherein the plurality of measurements is a subset of all of the measurements in the absence of processing.

13. The method of claim 1, wherein the plurality of measurements includes data that is representative of the original measurements after preprocessing for smoothing.

14. The method of claim 1, wherein the plurality of measurements includes a subset of data that is representative of the original measurements after preprocessing for smoothing.

15. The method of claim 1, wherein the plurality of measurements includes data that is representative of the original measurements after preprocessing by fitting to a function.

16. The method of claim 15, wherein the plurality of measurements includes a subset of data that is representative of the original measurements after preprocessing by fitting to a function.

17. An in vitro method of determining an analyte concentration of a sample, the method comprising the acts of:
    placing the sample into a low-field, bench-top time-domain nuclear magnetic resonance (TD-NMR) spectrometer, the NMR spectrometer being tuned to measure a selected type of atom;
    applying a magnetic field to the sample using a fixed, permanent magnet;
    applying at least one 90 degree radio-frequency pulse to the sample, the radio-frequency pulse being generally perpendicular to the magnetic field;
    removing the 90 degree radio-frequency pulse from the sample so as to produce a decaying NMR signal;
    measuring the decaying NMR signal at a plurality of times while applying a plurality of 180 degree refocusing radio-frequency pulses to the sample; and
    calculating the analyte concentration from the plurality of measurements associated with the decaying NMR signal and a selected model,
    wherein the selected model is a multivariate calibration model.

18. The method of claim 17, wherein the multivariate calibration model uses a chemometric technique.

19. The method of claim 18, wherein the chemometric technique uses partial least squares (PLS).

20. The method of claim 18, wherein the chemometric technique uses principal components regression (PCR).

* * * * *